US009144792B2

(12) United States Patent
Kiss et al.

(10) Patent No.: US 9,144,792 B2
(45) Date of Patent: Sep. 29, 2015

(54) HYDROALKYLATING PROCESS (71) Applicant: ExxonMobil Chemical Patents Inc., Baytown, TX (US)

(72) Inventors: Gabor Kiss, Hampton, NJ (US); Thomas E. Green, Hamilton, NJ (US); Terry E. Helton, Bethlehem, PA (US); Tan-Jen Chen, Kingwood, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 14/498,495

(22) Filed: Sep. 26, 2014

(65) Prior Publication Data
US 2015/0112098 A1 Apr. 23, 2015

Related U.S. Application Data (60) Provisional application No. 61/894,703, filed on Oct. 23, 2013.

(30) Foreign Application Priority Data

Jan. 21, 2014 (EP) .................................... 14151847

(51) Int. Cl.
C07C 45/53 (2006.01)
C07C 37/08 (2006.01)
C07C 2/66 (2006.01)
B01J 29/00 (2006.01)
B01J 29/88 (2006.01)
C07C 2/74 (2006.01)
C07C 407/00 (2006.01)
B01J 23/40 (2006.01)
B01J 23/75 (2006.01)
B01J 23/755 (2006.01)
B01J 29/65 (2006.01)
B01J 29/70 (2006.01)
B01J 29/72 (2006.01)
B01J 29/80 (2006.01)
C07C 6/12 (2006.01)

(52) U.S. Cl.
CPC B01J 29/88 (2013.01); B01J 23/40 (2013.01); B01J 23/75 (2013.01); B01J 23/755 (2013.01); B01J 29/65 (2013.01); B01J 29/7038 (2013.01); B01J 29/7276 (2013.01); B01J 29/80 (2013.01); C07C 2/66 (2013.01); C07C 2/74 (2013.01); C07C 6/126 (2013.01); C07C 37/08 (2013.01); C07C 45/53 (2013.01); C07C 407/00 (2013.01); C07C 2529/00 (2013.01); C07C 2529/65 (2013.01); C07C 2529/88 (2013.01)

(58) Field of Classification Search
CPC .......... C07C 45/53; C07C 37/08; C07C 2/66; B01J 2229/42; B01J 29/7038; B01J 29/7088

USPC .................. 568/376, 798, 799; 585/268, 467; 502/64, 66
See application file for complete search history.

(56) References Cited

U.S. PATENT DOCUMENTS

| 4,439,409 | A | 3/1984 | Puppe et al. |
|---|---|---|---|
| 4,826,667 | A | 5/1989 | Zones et al. |
| 4,954,325 | A | 9/1990 | Rubin et al. |
| 5,190,736 | A | 3/1993 | Hellring et al. |
| 5,236,575 | A | 8/1993 | Bennett et al. |
| 5,250,277 | A | 10/1993 | Kresge et al. |
| 5,362,697 | A | 11/1994 | Fung et al. |
| 6,037,513 | A | 3/2000 | Chang et al. |
| 6,049,018 | A | 4/2000 | Calabro et al. |
| 6,077,498 | A | 6/2000 | Diaz Cabañas et al. |
| 6,720,462 | B2 | 4/2004 | Kuhnle et al. |
| 6,730,625 | B1 | 5/2004 | Chang et al. |
| 6,756,030 | B1 | 6/2004 | Rohde et al. |
| 7,579,511 | B1 | 8/2009 | Dakka et al. |
| 2008/0027259 | A1 | 1/2008 | Roth et al. |
| 2012/0277472 | A1* | 11/2012 | Dakka et al. .................. 568/376 |

FOREIGN PATENT DOCUMENTS

| EP | 0 293 032 | 11/1988 |
|---|---|---|
| WO | WO 96/41849 | 12/1996 |
| WO | WO 97/17290 | 5/1997 |
| WO | WO 2008/013639 | 1/2008 |
| WO | WO 2008/013644 | 1/2008 |
| WO | WO 2008/016456 | 2/2008 |
| WO | WO 2008/016477 | 2/2008 |
| WO | WO 2009/055216 | 4/2009 |
| WO | WO 2009/128984 | 10/2009 |
| WO | WO 2009/131769 | 10/2009 |
| WO | WO 2012/036822 | 3/2012 |
| WO | WO 2012/050751 | 4/2012 |
| WO | WO 2014/018251 | 1/2014 |

OTHER PUBLICATIONS

Corma et al., "Synthesis and characterization of the MCM-22 zeolite", Zeolites, Elsevier Science Publishing, US, vol. 15, No. 1, Jan. 1, 1995, pp. 2-8, XP004033780.
U.S. Appl. No. 61/712,980, entitled, "Activation and Use of Hydroalkylation Catalysts", filed on Oct. 12, 2012.
U.S. Appl. No. 61/892,712, entitled, "Hydroalkylating Process", filed on Oct. 18, 2013.
U.S. Appl. No. 61/736,581, entitled, "Alkylating Process", filed on Dec. 13, 2012.
U.S. Appl. No. 61/841,072, entitled, "Process for Concentrating a Mixture Containing Organic Hydroperoxide", filed on Jun. 28, 2013.
U.S. Appl. No. 61/804,957, entitled, "Process for Making Alkylated Aromatic Compound", filed on Mar. 5, 2013.
U.S. Appl. No. 61/804,962, entitled, "Process for Making Alkylated Aromatic Compound", filed on Mar. 25, 2013.

* cited by examiner

Primary Examiner — Sikarl Witherspoon
(74) Attorney, Agent, or Firm — Siwen Chen; Stephen A. Baehl (57) ABSTRACT Disclosed are a catalyst comprising (A) an aluminosilicate molecular sieve comprising a ferrierite phase and (B) a hydrogenation metal component, and a hydroalkylation process using the catalyst. The catalyst and the hydroalkylation process can be used in the production of phenol and/or cyclohexanone from benzene hydroalkylation.

23 Claims, 2 Drawing Sheets

FIG. 1

FIG. 2

HYDROALKYLATING PROCESS

PRIORITY CLAIM

This application claims priority to U.S. Provisional Application Ser. No. 61/894,703 filed Oct. 23, 2013, and European Application No. 14151847.2, filed Jan. 21, 2014, the disclosures of which are fully incorporated herein by their reference.

FIELD

The present invention relates to a process for hydroalkylating an aromatic compound. In particular, the present invention relates to a process for hydroalkylating benzene for making cyclohexylbenzene. The present invention is useful, e.g., in making phenol and cyclohexanone via the route of benzene hydroalkylation.

BACKGROUND

Phenol and cyclohexanone are important materials in the chemical industry and are useful in, for example, the production of phenolic resins, bisphenol A, ε-caprolactam, adipic acid, and plasticizers.

Currently, a common route for the production of phenol is the Hock process. This is a three-step process in which the first step involves alkylation of benzene with propylene to produce cumene, followed by oxidation of cumene to the corresponding hydroperoxide, and then cleavage of the hydroperoxide to produce equimolar amounts of phenol and acetone. However, the world demand for phenol is growing more rapidly than that for acetone. In addition, the cost of propylene feed is generally high.

Thus, a process that uses alternative feeds and coproduces higher-value ketones, such as cyclohexanone, rather than acetone may be an attractive alternative route to the production of phenols.

It is known from, e.g., U.S. Pat. No. 6,037,513 that cyclohexylbenzene can be produced by contacting benzene with hydrogen in the presence of a bifunctional catalyst comprising a molecular sieve of the MCM-22 type and at least one hydrogenation metal component selected from Pd, Ru, Ni, Co, and mixtures thereof. This reference also discloses that the resultant cyclohexylbenzene can be oxidized to the corresponding hydroperoxide which is then decomposed to the desired phenol and cyclohexanone co-product.

In the hydroalkylation step, both the conversion of the aromatic compound (e.g., benzene) and the selectivity of the target alkylated aromatic compound are substantially determined by the performance of the hydroalkylation catalyst. Hydroalkylation using a catalyst comprising MCM-22 molecular sieve and a hydrogenation metal component can result in quite substantial amounts of dicyclohexylbenzene and tricyclohexylbenzene due to over alkylation of cyclohexylbenzene. There is a need for an improved catalyst and hydroalkylation process that with reduced over alkylation without sacrificing cyclohexylbenzene yield.

SUMMARY

It has now been unexpectedly discovered that a hydroalkylation process using a catalyst comprising, in addition to an aluminosilicate molecular sieve and a hydrogenation metal component, a ferrierite phase resulted in reduced over-alkylation of cyclohexylbenzene without sacrificing cyclohexylbenzene yield. The present disclosure is based on this discovery.

Thus, a first aspect of the present disclosure relates to a catalyst comprising
(A) an aluminosilicate molecular sieve comprising a ferrierite phase; and
(B) a hydrogenation metal component.

The molecular sieve may be of an MWW type, preferably an MCM-22 type. The concentration of the ferrierite phase, expressed on the basis of the total weight of the molecular sieve, may range from 10 ppm to 5.0 wt %, preferably from 0.01 wt % to 0.50 wt %.

The molecular sieve may exhibit an X-ray diffraction pattern including d-spacing maxima at 12.4±0.25, 6.9±0.15, 3.57±0.07, and 3.42±0.07 Angstrom. The molecular sieve may exhibit an X-ray diffraction peak 2θ at 9.5±0.5 degrees.

A second aspect of the present disclosure relates to a hydroalkylation process comprising contacting a first aromatic compound with hydrogen in the presence of a catalyst according to the first aspect described above under hydroalkylation conditions to produce an alkylated aromatic compound.

The first aromatic compound may be benzene or alkylbenzene, and the alkylated aromatic compound may be cyclohexylbenzene, alkylcyclohexylbenzene, cyclohexylalkylbenzene, or alkylcyclohexyl alkylbenzene.

A third aspect of the present disclosure relates to a process for making phenol and/or cyclohexanone comprising:
(A) contacting benzene with hydrogen in the presence of a catalyst of the first aspect of the present disclosure under hydroalkylation conditions to obtain a hydroalkylation product comprising cyclohexylbenzene;
(B) oxidizing at least a portion of the cyclohexylbenzene in the hydroalkylation product to obtain an oxidation product comprising cyclohexylbenzene hydroperoxide; and
(C) cleaving at least a portion of the cyclohexylbenzene hydroperoxide in the oxidation product in the presence of an acid cleavage catalyst to obtain a cleavage product comprising phenol and cyclohexanone.

DETAILED DESCRIPTION

In the present disclosure, a process is described as comprising at least one "step." It should be understood that each step is an action or operation that may be conducted once or multiple times in the process, in a continuous or discontinuous fashion. Unless specified to the contrary or the context clearly indicates otherwise, the steps in a process may be conducted sequentially in the order as they are listed, with or without overlapping with one or more other step(s), or in any other order, as the case may be. In addition, two or more or even all steps may be conducted simultaneously with regard to the same or different batch of material. For example, in a continuous process, while a first step in a process is being conducted with respect to a raw material just fed into the beginning of the process, a second step may be conducted simultaneously with respect to an intermediate material resulting from treating the raw materials fed into the process at an earlier time in the first step. Preferably, steps are performed in the order as listed.

Unless otherwise indicated, all numbers indicating quantities in the present disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contain a certain level of error due to the limitation of the technique and equipment used for making the measurement.

As used herein, the indefinite article "a" or "an" shall mean "at least one" unless specified to the contrary or the context clearly indicates otherwise. Thus, embodiments using "a hydrogenation metal component" include embodiments where one, two or more different types of the hydrogenation metal component(s) are used, unless specified to the contrary or the context clearly indicates that only one type of the hydrogenation metal component is used.

As used herein, "wt %" means percentage by weight, "vol %" means percentage by volume, "mol %" means percentage by mole, "ppm" means parts per million, and "ppm wt" and "wppm" are used interchangeably to mean parts per million on a weight basis. All "ppm" as used herein are ppm by weight unless specified otherwise. All concentrations herein are expressed on the basis of the total amount of the composition in question unless specified or indicated otherwise. All ranges expressed herein should include both end points as two specific embodiments unless specified or indicated to the contrary.

As used herein, the generic term "dicylcohexylbenzene" includes, in the aggregate, 1,2-dicyclohexylbenzene, 1,3-dicylohexylbenzene, and 1,4-dicycloxylbenzene, unless clearly specified to mean only one or two thereof. The term cyclohexylbenzene, when used in singular form, means mono substituted cyclohexylbenzene.

As used herein, the generic term "phenylcyclohexene" includes, in the aggregate, 2-phenyl-1-cyclohexene, 3-phenyl-1-cyclohexene, and 4-phenyl-1-cyclohexene, unless clearly specified to mean only one or two thereof.

The term "MCM-22 type material" (or "material of the MCM-22 type," "molecular sieve of the MCM-22 type," or "MCM-22 type zeolite"), as used herein, includes one or more of:

molecular sieves made from a common first degree crystalline building block unit cell, which unit cell has the MWW framework topology. A unit cell is a spatial arrangement of atoms which if tiled in three-dimensional space describes the crystal structure. Such crystal structures are discussed in the "Atlas of Zeolite Framework Types," Fifth Edition, 2001, the entire content of which is incorporated as reference;

molecular sieves made from a common second degree building block, being a 2-dimensional tiling of such MWW framework topology unit cells, forming a monolayer of one unit cell thickness, desirably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of the MCM-22 type include those molecular sieves having an X-ray diffraction pattern including d-spacing maxima at 12.4±0.25, 6.9±0.15, 3.57±0.07, and 3.42±0.07 Angstrom. The X-ray diffraction data used to characterize the material are obtained by standard techniques such as using the K-alpha doublet of copper as incident radiation and a diffractometer equipped with a scintillation counter and associated computer as the collection system.

Materials of the MCM-22 type include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), and mixtures thereof. Other molecular sieves, such as UZM-8 (described in U.S. Pat. No. 6,756,030), may be used alone or together with the MCM-22 type molecular sieves as well for the purpose of the present disclosure. Desirably, the molecular sieve is selected from (a) MCM-49; (b) MCM-56; and (c) isotypes of MCM-49 and MCM-56, such as ITQ-2.

The catalyst of the present disclosure comprises an aluminosilicate molecular sieve comprising a ferrierite phase, a hydrogenation metal component optionally an inorganic oxide support component, and optionally a binder. As such, the catalyst can be bifunctional, i.e., capable of catalyzing both the hydrogenation reaction and an alkylation reaction, and thus can be advantageously used in hydroalkylation reactions, especially hydroalkylation reactions of aromatic compounds such as benzene and derivatives thereof.

The aluminosilicate molecular sieve contained in the catalyst of the present disclosure comprises a predominant component different from ferrierite, which can be, e.g., a molecular sieve of the following types: zeolite beta, zeolite X, zeolite Y, mordenite and zeolites of the MWW framework type (see "Atlas of Zeolite Framework Types", Fifth edition, 2001), and mixtures and combinations thereof. As examples of molecular sieves of the MWW framework type, MCM-22 type molecular sieves described above are particularly advantageous. In one practical example, the molecular sieve of the MWW framework type is MCM-22 or MCM-49. The predominant component of the aluminosilicate molecular sieve used in the catalyst may be characterized by an X-ray diffraction pattern including d-spacing maxima at 12.4±0.25, 6.9±0.15, 3.57±0.07, and 3.42±0.07 Angstrom. The predominant component of the molecular sieve can constitute at least 90%, 91%, 92%, 93%, 94%, 95%, 96%, 97%, 98%, 99%, 99.9%, 99.99%, 99.999%, or even higher percentage, of the total weight of the aluminosilicate molecular sieve.

The aluminosilicate molecular sieve contained in the catalyst of the present disclosure comprises a ferrierite phase detectable by X-ray diffraction as a minor phase. In a surprising manner, it was found that the presence of the ferrierite phase, even at a small concentration, was conducive to the catalytic effect of the catalyst, especially in terms of selectivity of heavy components in hydroalkylation reactions of aromatic compounds. Without intending to be bound by a particular theory, it is believed that the presence of the ferrierite phase in the molecular sieve induces structure changes in the molecular sieve that would result in lower probability of additional alkylation reaction between a cyclic alkyl aromatic compound and an olefin. However, it is believed that, if the concentration of the ferrierite phase is overly high, the alkylation reaction, catalyzed by the molecular sieve, can be reduced to an undesirable level such that the selectivity toward the desired alkylated aromatic compound becomes too low. Thus, the catalyst of the present disclosure can comprise the ferrierite phase at a concentration expressed on the basis of the total weight of the aluminosilicate molecular sieve, in a range from A1 ppm to A2 ppm by weight, where A1 and A2 can be, independently, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 15000, 20000, 25000, 30000, 35,000, 40000, 45000, 50000, as long as A1<A2. Thus, the catalyst of the present disclosure can comprise any one of Na, K, Ca, Mg at a concentration expressed on the basis of the total weight of the aluminosilicate molecular sieve, in a range from B1 ppm to B2 ppm by weight, where B1 and B2 can be, independently, 5, 10, 20, 30, 40, 50, 60, 70, 80, 90, 100, 200, 300, 400, 500, 600, 700, 800, 900, 1000, 2000, 3000, 4000, 5000, as long as B1<B2. In an advantageous embodiment, the catalyst of the present disclosure can comprise Na at a concentration expressed on the basis of the total weight of the aluminosilicate molecular sieve, in a range from C1 ppm to C2 ppm by weight, where C1 and C2 can be, independently, 5, 10, 20, 30, 40, 50, 60, 70, 80, 90, 100, 200, 300, 400, 500, 600, 700, 800, 900, 1000, 2000, 3000, 4000, 5000, as long as C1<C2, and the catalyst comprises K, Ca, and Mg each at a centration expressed on the basis of the total weight of the aluminosilicate molecular sieve of at most 100 ppm (or at most 80, 70, 60, 50, 40, 30, 20, 10 ppm).

Figure 1:
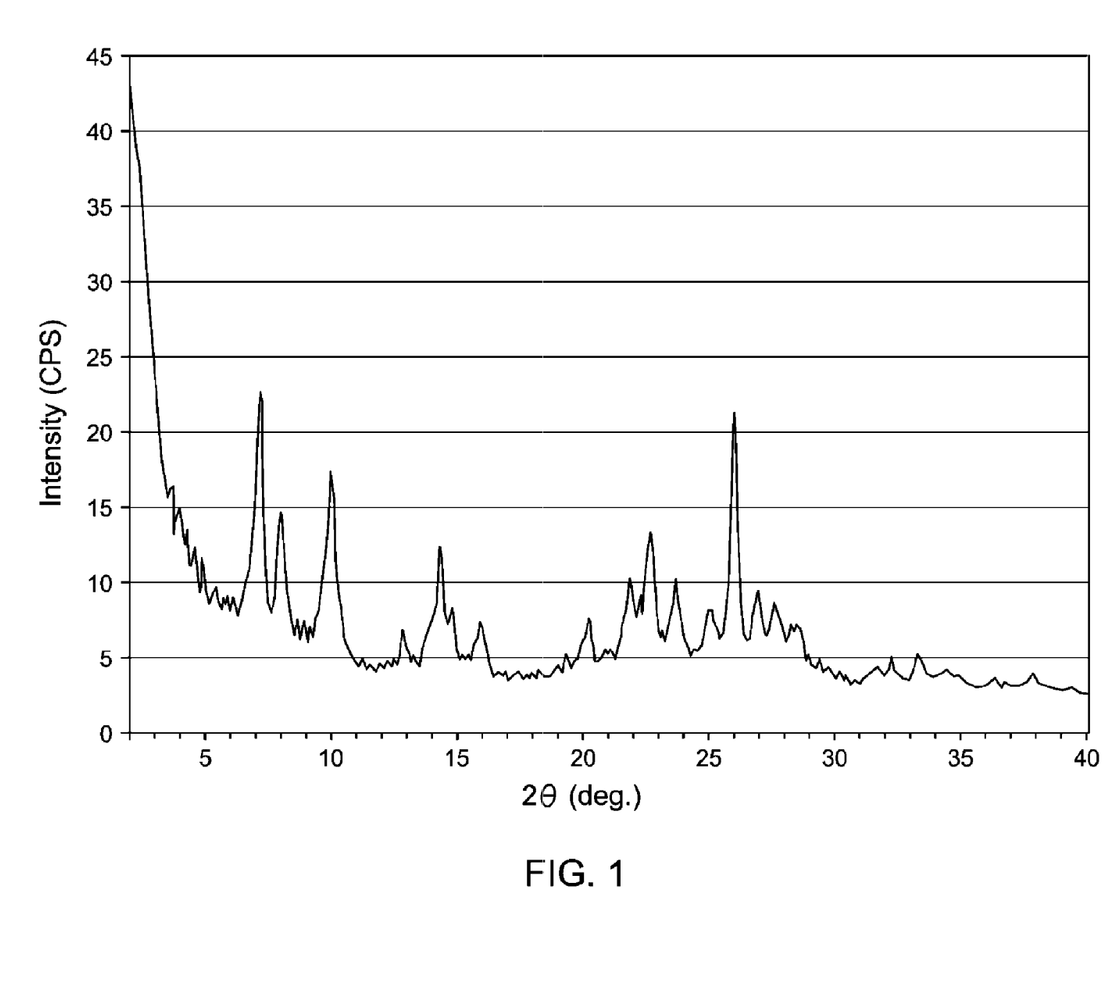
FIG. 1 is an X-ray diffraction diagram of a comparative catalyst comprising MCM-49 molecular sieve, $Al_2O_3$ and Pd.
Figure 2:
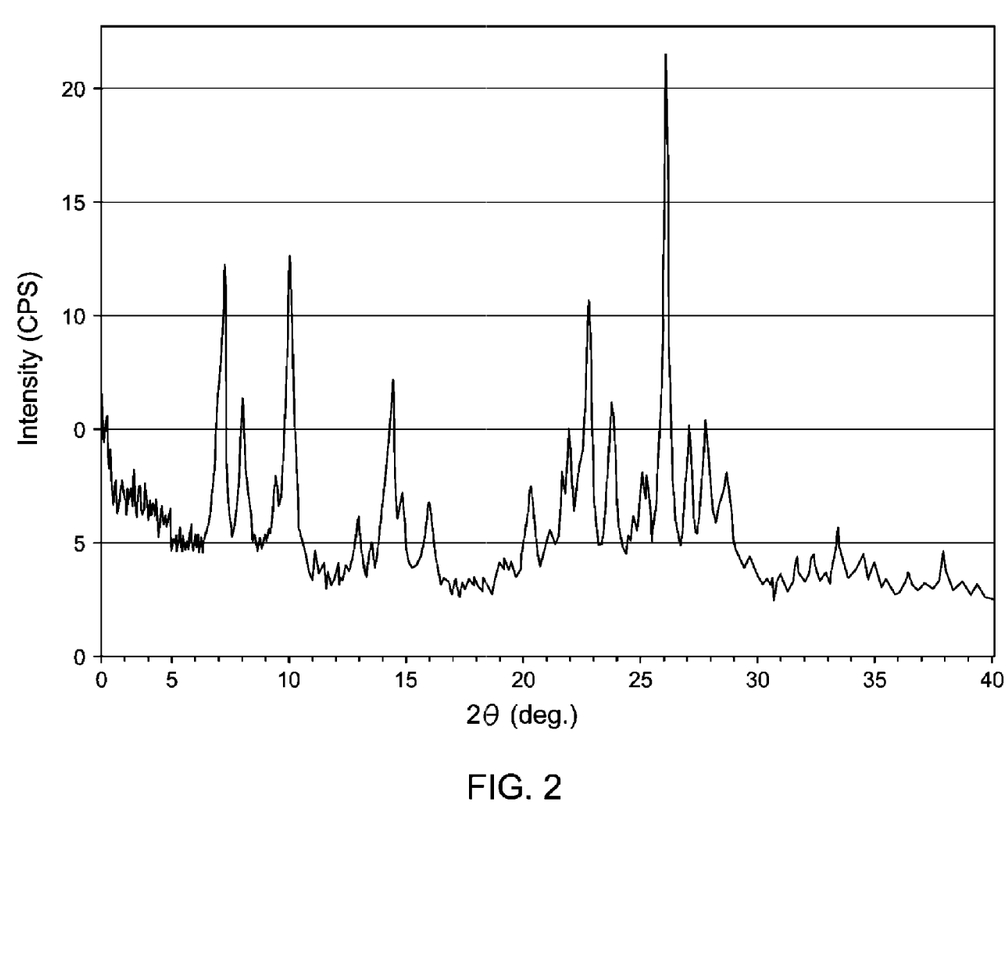
FIG. 2 is an X-ray diffraction diagram of an example of the currently disclosed catalysts comprising MCM-49 molecular sieve, a ferrierite phase, $Al_2O_3$ and Pd.

FIG. 1 is an XRD (X-Ray Diffraction) diagram of a comparative catalyst comprising 0.15 wt % Pd, 20 wt % $Al_2O_3$, and 80 wt % MCM-49 showing no appreciable 2θ peak at location of 9.5±0.5 degrees. FIG. 2 is an XRD diagram of an inventive catalyst according to the present disclosure comprising 0.15 wt % Pd, 20 wt % $Al_2O_3$, and 80 wt % MCM-49 showing an appreciable 2θ peak at location of 9.5±0.5 degrees. The 2θ peak at 9.5±0.5 degrees is indicative of the presence of the ferrierite phase.

Ferrierite is a specific type of aluminosilicate molecular sieve comprising one or more alkali or alkali earth metals such as Na, K, Ca, Mg, and the like. The ferrierite phase in the molecular sieve in the catalyst of the present disclosure may be intentionally supplied as a ferrierite molecular sieve per se as part of the starting materials for making the catalyst, and included in or combined with one or more of the supplies of the molecular sieve, the inorganic support component, and the optional binder. For example, the ferrierite phase can be produced in the process of making the primary phase of the aluminosilicate molecular sieve. For example, in the process of making MCM-49 molecular sieve involving using NaOH as the pH adjuster, prolonged crystallization time can lead to the formation of a minor Na-ferrierite phase mixed with MCM-49 crystals. Alternatively, the ferrierite phase can be produced in situ in the process of making the catalyst of the present disclosure. For example, a desired amount of a source material (such as a salt or hydroxide) of the alkali and/or alkali earth metal(s) to be included in the ferrierite phase may be combined with one or more of the source materials of the molecular sieve, the inorganic oxide support component, and the binder, such that a catalyst precursor formed from these source material contains the alkali and/or alkali earth metal(s), which, upon further treatment including but not limited to drying, heating (calcination, e.g.), and activation, undergo in-situ chemical reactions to form the ferrierite phase at desirable amounts.

Any known hydrogenation metal can be employed in the catalyst of the present disclosure. Particularly advantageous examples of the hydrogenation metal component include Pd, Pt, Ru, Fe, Rh, Os, Ir, Ni, Zn, Sn, and Co, with Pd and Pt being especially desirable. Thus, the amount of hydrogenation metal component present in the hydroalkylation catalyst may be in a range from Chma1 wt % to Chma2 wt %, based on the total weight of the hydroalkylation catalyst, where Chma1 and Chma2 can be, independently, 0.01, 0.02, 0.03, 0.04, 0.05, 0.06, 0.07, 0.08, 0.09, 0.10, 0.12, 0.15, 0.20, 0.25, 0.30, 0.35, 0.40, 0.45, 0.50, 0.60, 0.70, 0.80, 0.90, 1.0, 2.0, 3.0, 4.0, 5.0, 6.0, 7.0, 8.0, 9.0, or even 10.0, as long as Chma1<Chma2. The molar ratio of the aluminum in the molecular sieve to the hydrogenation metal component may be in a range from 1.5 to 1500, for example in a range from 30 to 750, or in a range from 75 to 750, such as in a range from 30 to 300.

The hydrogenation metal component may be directly supported on the molecular sieve by, for example, impregnation or ion exchange, or can be supported on the inorganic oxide support component (if present), or both. Thus, at least A1 wt % of the hydrogenation metal component may be supported on an inorganic oxide support component separate from but composited with the molecular sieve, where the percentage is based on the total weight of the hydroalkylation catalyst, and A1 can be: 50, 55, 60, 75, 80, 85, 90, 95, 98, 99, or even 99.5. By supporting a majority of the hydrogenation metal component on the inorganic oxide support component, the activity of the catalyst and its selectivity to cyclohexylbenzene, dicyclohexylbenzene, and tricyclohexylbenzene in the hydroalkylation reaction are increased as compared with an equivalent catalyst in which the hydrogenation metal component is supported directly on the molecular sieve.

The inorganic oxide support component contained in such a composite hydroalkylation catalyst is not narrowly defined provided it is stable and inert under the conditions of the hydroalkylation reaction. Suitable inorganic oxides include oxides of elements in Groups 2, 3, 4, 5, 13, and 14 of the Periodic Table of Elements. Examples of suitable and widely available inorganic oxides include, for example, alumina, silica, silica-alumina, titania, zirconia, and combinations and mixtures thereof. As used herein, the numbering scheme for the Periodic Table Groups is as disclosed in Chemical and Engineering News, 63(5), 27 (1985). The inorganic oxide support component, when included in the catalyst, may have an average particle size in the catalyst in a range from 1 µm to 70 µm, or from 2 µm to 60 µm, or from 5 µm to 50 µm, or from 6 µm to 40 µm. The average particle size of the inorganic oxide support component in the final catalyst may be represented by the average particle size of the inorganic oxide component before it is combined with other catalyst source materials such as molecular sieve and hydrogenation metal.

Loading the hydrogenation metal component on the inorganic oxide support can be conveniently effected by impregnation of the inorganic oxide support component with a solution of a salt of the desired hydrogenation metal component, which can be followed by drying and optional calcination and then compositing with the molecular sieve such as a MWW type molecular sieve. For example, the catalyst composite can be produced by co-pelletization, in which a mixture of the molecular sieve and the metal-containing inorganic oxide support is formed into pellets at high pressure (e.g., from 350 kPa to 350,000 kPa), or by co-extrusion, in which a slurry of the molecular sieve and the metal-containing inorganic oxide support, optionally together with a separate binder, which can be organic or inorganic, are forced through a die. Examples of inorganic binder materials are described below. If necessary, additional amount of the hydrogenation metal component can be subsequently deposited on the resultant catalyst composite. Drying can be carried out at a temperature in a range from Td1° C. to Td2° C., where Td1 and Td2 can be, independently, 20, 25, 30, 35, 40, 45, 50, 55, 60, 65, 70, 80, 90, 100, 110, 120, 130, 140, 150, 160, 170, 180, 190, 200, 210, 220, 230, 240, 250, 260, 270, 280, 290, or 300, as long as Td1<Td2. Calcination can be conducted at a temperature in a range from Tc1° C. to Tc2° C., where Tc1 and Tc2 can be, independently, 100, 110, 120, 130, 140, 150, 160, 170, 180, 190, 200, 210, 220, 230, 240, 250, 260, 270, 280, 290, 300, 350, 400, 450, 500, 550, 600, 650, 700, 750, 800, 850, 900, 950, 1000, as long as Tc1<Tc2. Calcination can be conducted advantageously in an atmosphere comprising $O_2$, such as air, so that organic matters contained in the catalyst source materials are burned, reduced or eliminated.

Alternatively, the molecular sieve is first extruded with the inorganic oxide component. The thus obtained substrate is dried and optionally calcined, and then the hydrogenation metal component is impregnated into the substrate, followed by drying and optional calcination. In this case, the impregnation conditions can be adjusted such that the hydrogenation metal component is preferentially associated with the oxide component of the extrudate. Drying and calcination may be conducted as described above.

The hydroalkylation catalyst may further comprise an optional inorganic binder, non-limiting examples of which include clay, silica and/or metal oxides. Naturally occurring clays which can be used as a binder include those of the montmorillonite and kaolin families, which families include the subbentonites and the kaolins commonly known as Dixie, McNamee, Ga., and Florida clays or others in which the main mineral constituent is halloysite, kaolinite, dickite, nacrite or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia, and silica-magnesia-zirconia. The binder mechanically connects catalytically active particles comprising the hydrogenation metal component, the solid acid, and optionally an inorganic oxide support component into a larger body, such as a pellet, a cylinder, a pill, and the like, which can be convenient loaded into a hydroalkylation reactor.

After the incorporation of the hydrogenation metal component, the molecular sieve, optionally the inorganic oxide support component, and optionally the binder, a catalyst precursor of the hydroalkylation catalyst is formed. After calcination, the hydrogenation metal component is normally in an inactive oxidized form in the precursor and therefore, before being employed in a hydroalkylation process, the resultant catalyst precursor is desirably activated to convert at least some of the hydrogenation metal component content to its zero-valent elemental state. For example, in a Pt-containing catalyst, the Pt would take the form of $PtO_2$ if the precursor has been calcined in the presence of $O_2$. During the activation step, the following Reaction-5 takes place:

$$PtO_2 + 2H_2 \rightarrow Pt + 2H_2O \qquad \text{(Reaction-5)}.$$

The activation process can be conducted by heating the catalyst precursor in the presence of hydrogen in, e.g., the same reactor as that used for the subsequent hydroalkylation step. However, if desired, the activation may be conducted in one or more separate reactors and the activated catalyst is subsequently transferred to the hydroalkylation reactor. Desirably, the activation atmosphere comprises a flowing stream of dry $H_2$-containing gas such that the water produced during the activation reaction above is carried away.

Activation processes for the precursor of hydroalkylation catalysts are described in: co-pending, co-assigned PCT application No. PCT/US2013/049720, filed on Jul. 9, 2013 and entitled "Activation and Use of Hydroalkylation Catalysts;" U.S. Provisional Application Ser. No. 61/712,980, filed on Oct. 12, 2012 and entitled "Activation and Use of Hydroalkylation Catalysts;" WO2012/050751; and U.S. Provisional Application Ser. No. 61/892,712, filed on Oct. 18, 2013 and entitled "Hydroalkylating Process," the contents of all of which are incorporated herein by reference.

A hydroalkylation process according to the present disclosure may involve a gaseous phase comprising hydrogen, a first aromatic compound subjected to hydroalkylation (desirably partially in liquid phase), and a hydroalkylation reaction taking place in the presence of the catalyst of the present disclosure.

In the process of the present disclosure, the first aromatic compound supplied to the hydroalkylation reactor may have the following general formula (F-I):

(F-I)

where:

$R^1$, the same or different at each occurrence, each independently represents a substituted or unsubstituted linear, branched acyclic, or cyclic alkyl or alkenyl group having from 1 to 20 carbon atoms (such as 1 to 10, or 1 to 5 carbon atoms); and m is an integer from 0 to 5, preferably 0 or 1.

Non-limiting examples of such aromatic compounds include: benzene, toluene, ethylbenzene, n-propylbenzene, cumene, n-butylbenzene, 2-phenylbutane, o-xylene, m-xylene, p-xylene, o-methylethylbenzene, m-methylethylbenzene, p-methylethylbenzene, and the like.

Thus, a desired product in the reaction effluent of the alkylation process can be an alkylated aromatic compound represented by the following general formula (F-II):

(F-II)

where:

$R^2$ and $R^3$, the same or different at each occurrence, each independently represents a substituted or unsubstituted linear, branched acyclic, or cyclic alkyl or alkenyl having from 1 to 20 carbon atoms (such as from 1 to 10, or from 1 to 5); and o and p are independently integers from 0 to 5; preferably, o and p are independently 0 or 1.

Non-limiting examples of compounds having formula (F-II) include:
cyclohexylbenzene;
methylcyclohexyltoluene;
methylcyclohexyl-ethylbenzene;
ethylcyclohexyl-ethylbenzene;
propylcyclohexyl-propylbenzene;

butylcyclohexyl-butylbenzene;
dimethylcyclohexyl-dimethylbenzene;
diethylcyclohexyl-diethylbenzene;
trimethylcyclohexyl-trimethylbenzene;
isopropylcyclohexylcumene;
methylethylcyclohexyl-methylethylbenzene; and
combinations and mixtures of at least two thereof.

In hydroalkylation of benzene with hydrogen to produce cyclohexylbenzene, a $H_2$-containing gas feed and a liquid benzene-containing liquid feed may be charged into the hydroalkylation reactor, where the following reactions, among others, may take place on the surface of a bi-functional hydroalkylation catalyst comprising a hydrogenation metal component such as Pd and a molecular sieve such as a molecular sieve of the MCM-22 type:

During the hydroalkylation reaction, in the hydroalkylation reactor, the activated hydroalkylation catalyst is located in a first reaction zone. Thus, the feed materials including the first aromatic compound such as, for example, benzene, and hydrogen, are mixed and allowed to contact the activated hydroalkylation catalyst. Desirably, the feed materials are fed into the hydroalkylation reactor from the top and then flow downward through a bed of the activated hydroalkylation catalyst due to gravity and pressure gradient. On contacting the hydrogenation metal component and molecular sieve, the first aromatic compound and hydrogen react to produce a hydroalkylation reaction mixture comprising hydrogen, an alkylated aromatic compound, such as, for example, cyclohexylbenzene in the case of benzene hydroalkylation, and optionally other compounds, such as olefins.

The hydroalkylation reaction mixture may be subjected to additional treatment such as hydrogenation in a downstream second reaction zone of the same hydroalkylation reactor, which is located below the first reaction zone if the first aromatic compound and hydrogen feed(s) are supplied from the top of the hydroalkylation reactor. Such additional treatment may include, e.g., hydrogenation by contacting with a layer of hydrogenation catalyst. The optionally additionally treated hydroalkylation reaction mixture can then exit the hydroalkylation reactor as one or more streams. Where multiple streams exited the hydroalkylation reactor, those streams may have the same or different compositions. For example, one stream may comprise more hydrogen than the other.

It has been found that the molar ratio of hydrogen gas to the first aromatic compound fed into the reactor partly determines the extent to which desired and undesired reactions take place on the catalyst. For example, in the case of hydroalkylation of benzene, where there is a substantial oversupply of $H_2$, more cyclohexane bicyclohexylbenzene may be produced; and in the case of a substantial oversupply of benzene, more biphenyls may be produced. In a hydroalkylation reaction where the target product is cyclohexylbenzene, all by-products cyclohexane, biphenyl, and bicyclohexane are undesired and should be minimized. Therefore, the molar ratio of $H_2$ to benzene is desired to be within a given range in the feed materials, such as from RM1 to RM2, where RM1 can be 0.01, 0.05, 0.10, 0.15, 0.20, 0.25, 0.30, 0.35, 0.40, 0.45, 0.50, 0.60, 0.80, 1.00, and RM2 can be 15.0, 10.0, 8.0, 6.0, 4.0, 2.0, 1.5, 1.0, 0.90, 0.80, 0.70, 0.60, as long as RM1<RM2. Desirably, RM1 is 0.10, and RM2 is 1.5.

It is highly desired that the first aromatic compound fed into the hydroalkylation reactor is in at least partly in liquid state, while hydrogen is supplied into the hydroalkylation reactor as a stream of gas containing hydrogen gas and optionally an inert gas such as methane. The two feed materials may be combined before or immediately after entering the hydroalkylation reactor.

The process according to the present disclosure may be conducted in a fixed-bed catalyst reactor, where the catalyst particles are packed inside a column, and the gas and liquid materials are allowed to travel, e.g., in a direction from the top to bottom, in contact with the surface of the hydroalkylation catalyst particles and the hydrogenation catalyst particles, whereby the hydroalkylation and/or hydrogenation reactions take place.

In the process of the present disclosure, both hydrogen and the first aromatic compound can be fed into the hydroalkylation reactor from a location above the bed of the hydroalkylation catalyst, mix together and travel through the hydroalkylation catalyst bed in an upper first reaction zone, produces a first reaction mixture, which travels downward through a second bed of hydrogenation catalyst and is converted into a second reaction mixture, and the second reaction mixture exits the hydroalkylation reactor at locations in proximity to the bottom of the bed of the hydrogenation catalyst, such as locations below the bottom of the bed of the catalyst. This down-flow configuration is particularly advantageous for carrying out gas-liquid reaction on the surface of a solid catalyst bed and can allow for a substantially uniform distribution of both liquid and gas in a horizontal cross-section of the solid catalysts. In such reactors, the liquid is first dispensed onto the upper surface of the hydroalkylation catalyst, then flows down the bed along the boundary of the catalyst particles, wet the surface of the catalyst particles in the bed along its way, and undergoes the desired reaction(s). A substantially uniform distribution of the liquid reaction media inside the bed of the catalyst is highly desired to control the amount of by-products produced inside the reactor. It was found that the distribution of the liquid fed into the reactor to the upper surface of the bed of the catalyst can significantly impact the distribution of the liquid reaction medium in the bulk of the bed of the catalyst. To achieve a substantially uniform distribution of the liquid reaction medium in the bulk, it is highly desired that the liquid fed into to the reactor is distributed substantially uniformly to the upper surface of the bed.

In the processes of the present disclosure, at least a portion of both of hydrogen and the first aromatic compound can be fed into the hydroalkylation reactor are supplied to the reactor at the same horizontal level of the reactor. Hydrogen and the first aromatic compound may be mixed and then fed into the hydroalkylation reactor together via the same port(s). Alternatively, hydrogen and the first aromatic compound are fed into the reactor via different, separate ports. At least some of the ports through each of which hydrogen and/or the first aromatic compound are fed into the reactor are above the upper surface of the bed of the hydroalkylation catalyst. To facilitate a substantially uniform distribution of the liquid aromatic compound feed material to the upper surface of the bed of the hydroalkylation catalyst, a plurality of ports may be used above the upper surface of the hydroalkylation catalyst bed, through each of which a portion of the total liquid feed is delivered into the reactor. Generally, it is easier to achieve a substantially uniform distribution of the hydrogen gas in the space above the upper surface of the bed of the hydroalkylation catalyst than the liquid aromatic compound feed material. Nonetheless, to ensure such uniform distribution of hydrogen gas, multiple ports for feeding gas may be used above the upper surface of the bed of the hydroalkylation catalyst as well.

It has been found that, in order to achieve a substantially uniform distribution of the liquid feed material in the space immediately above the upper surface of the bed of the catalyst, a fluid distributing device may be desired between the inlet of the liquid and the upper surface of the bed of the catalyst. Such fluid distributing device receives the liquid material fed into the reactor through the inlet(s), redirects the flow thereof in multiple horizontal directions, and eventually delivers the liquid into the space above the upper surface of the bed in the form of liquid droplets. Detailed description of fluid distributing devices suitable for the process of the present disclosure can be found in co-pending, co-assigned U.S. provisional patent application Ser. No. 61/736,581, filed on Dec. 13, 2012 and entitled "Alkylating Process," the content of which is incorporated herein by reference in its entirety. The temperature inside the hydroalkylation reactor can be monitored by using one or more temperature sensors. To control the temperature inside the reactor, the feed can be adjusted by increasing or reducing the amount of the first aromatic and/or hydrogen supplied. Advantageously, the amount of the first aromatic compound can be changed to quickly control the amount of heat generated from the hydrogenation reaction(s) and alkylation reaction(s).

The present invention can be advantageously employed in the process for making phenol and/or cyclohexanone via benzene hydroalkylation. Detailed description of the process is provided as follows.

Production of Cyclohexylbenzene

In the integrated process for producing phenol and cyclohexanone from benzene, the benzene can be initially converted to cyclohexylbenzene by any conventional technique, including alkylation of benzene with cyclohexene in the presence of an acid catalyst, such as zeolite beta or an MCM-22 type molecular sieve, or by oxidative coupling of benzene to make biphenyl followed by hydrogenation of the biphenyl. However, in practice, the cyclohexylbenzene is desirably produced by contacting the benzene with hydrogen under hydroalkylation conditions in the presence of a hydroalkylation catalyst whereby the benzene undergoes the following Reaction-5 to produce cyclohexylbenzene (CHB) according to a process of the present disclosure:

(Reaction-5)

U.S. Pat. Nos. 6,730,625 and 7,579,511, WO2009/131769, and WO2009/128984 disclose processes for producing cyclohexylbenzene by reacting benzene with hydrogen in the presence of a hydroalkylation catalyst, the contents of all of which are incorporated herein by reference in their entirety.

Although the benzene hydroalkylation reaction is highly selective towards cyclohexylbenzene, the effluent from the hydroalkylation reaction may contain some dialkylated products, unreacted benzene and cyclohexane. The unreacted benzene may be recovered by distillation and recycled to the reactor. The lower effluent from the benzene distillation may be further distilled to separate the monocyclohexylbenzene product from dicyclohexylbenzene and other heavies. Depending on the quantity of dicyclohexylbenzene present in the reaction effluent, it may be desirable to either (a) transalkylate the dicyclohexylbenzene with additional benzene or (b) dealkylate the dicyclohexylbenzene to maximize the production of the desired monoalkylated species.

Transalkylation with additional benzene is desirably effected in a transalkylation reactor, separate from the hydroalkylation reactor, over a suitable transalkylation catalyst, such as a molecular sieve of the MCM-22 type, zeolite beta, MCM-68 (see U.S. Pat. No. 6,014,018), zeolite Y, zeolite USY, and mordenite. The transalkylation reaction is desirably conducted under at least partial liquid phase conditions, which suitably include a temperature of 100° C. to 300° C., a pressure of 800 kPa to 3500 kPa, a weight hourly space velocity of 1 hr$^{-1}$ to 10 hr$^{-1}$ on total feed, and a benzene/dicyclohexylbenzene weight ratio of 1:1 to 5:1.

Oxidation of Cyclohexylbenzene

After removal of the unreacted benzene and the polyalkylated benzenes and other heavy species, the cyclohexylbenzene produced in the hydroalkylation step is fed to an oxidizing step, which can be conducted in one or more oxidation reactor(s). Desirably, at least a portion of the cyclohexylbenzene contained in the oxidation feed is converted to cyclohexyl-1-phenyl-1-hydroperoxide, the desired hydroperoxide according to the following Reaction-6:

(Reaction-6)

A feed supplied to the oxidizing step may comprise cyclohexylbenzene at a concentration in a range from C1 wt % to C2 wt %, based on the total weight of the feed introduced into the oxidation reactor, where C1 and C2 can be, independently,

10, 20, 30, 40, 50, 60, 70, 80, 90, 92, 94, 95, 96, 97, 98, 99, 99.5, or even 99.9, or even higher, as long as C1<C2. In addition, the feed to the oxidizing step may contain, based on the total weight of the feed, one or more of the following: (i) bicyclohexane at a concentration in a range from at 1 ppm to 1 wt %, such as from 10 ppm to 8000 ppm; (ii) biphenyl at a concentration in a range from 1 ppm to 1 wt %, such as from 10 ppm to 8000 ppm; (iii) phenylmethylcyclopentane, including one or more of 1-phenyl-1-methylcyclopentane, 1-phenyl-2-methylcyclopentane, and 1-phenyl-3-methylcyclopentane, at a total concentration in a range from 1 ppm to 2 wt %, such as from 10 ppm to 1 wt %; (iv) phenol at a concentration no greater than 1000 ppm, such as no greater than 100 ppm; and (v) olefins or alkene benzenes such as phenylcyclohexene at no greater than 1000 ppm (or no greater than 800, 600, 500, 400, 300, 200, 100, 80, 60, 50, 40, 20, 10, 8, 6, 5, 4, 2, 1 ppm), which is advantageously reduced by using the process of the present disclosure.

The oxidizing step may be accomplished by contacting an oxygen-containing gas, such as air and various derivatives of air, with the feed comprising cyclohexylbenzene. For example, a stream of pure $O_2$, air, or other $O_2$-containing mixtures may be pumped through the cyclohexylbenzene-containing feed in an oxidation reactor such as a bubble column to effect the oxidation.

The oxidation may be conducted in the absence or presence of a catalyst. Examples of suitable oxidation catalysts include those having a structure of formula (FC-I), (FC-II), or (FC-III) below:

(FC-I)

(FC-II)

(FC-III)

where:

A represents a ring optionally comprising a nitrogen, sulfur, or oxygen in the ring structure, and optionally substituted by an alkyl group, an alkenyl group, a halogen, or a N—, S—, or O-containing group or other group;

X represents a hydrogen, an oxygen, a hydroxyl group, or a halogen;

$R^1$, the same or different at each occurrence, independently represents a halogen, a N—, S—, or O-containing group, or a linear or branched acyclic alkyl or cyclic alkyl group having 1 to 20 carbon atoms, optionally substituted by an alkyl, an alkenyl, a halogen, or a N—, S—, or O-containing group or other group; and m is 0, 1 or 2.

Examples of particularly suitable catalysts for the oxidation step include those represented by the following formula (FC-IV):

(FC-IV)

where:

$R^2$, the same or different at each occurrence, independently represents a halogen, a N—, S—, or O-containing group, or a linear or branched acyclic alkyl or cyclic alkyl group having 1 to 20 carbon atoms, optionally substituted by an alkyl group, an alkenyl group, a halogen, a S—, O—, or N-containing group, or any other group; and n is 0, 1, 2, 3, or 4.

Especially suitable catalyst having the above formula (FC-IV) for the oxidation step is NHPI (N-hydroxy phthalic imide). Other suitable catalysts are described in U.S. Pat. No. 6,720,462, which is incorporated herein by reference. Specific, non-limiting examples of other suitable catalysts include: 4-amino-N-hydroxyphthalimide; 3-amino-N-hydroxyphthalimide, tetrabromo-N-hydroxyphthalimide; tetrachloro-N-hydroxyphthalimide; N-hydroxyhetimide; N-hydroxyhimimide; N-hydroxytrimellitimide; N-hydroxybenzene-1,2,4-tricarboximide; N,N'-dihydroxy(pyromellitic diimide); N,N'-dihydroxy(benzophenone-3,3', 4,4'-tetracarboxylic diimide); N-hydroxymaleimide; pyridine-2,3-dicarboximide; N-hydroxysuccinimide; N-hydroxy (tartaric imide); N-hydroxy-5-norbornene-2,3-dicarboximide; exo-N-hydroxy-7-oxabicyclo[2.2.1]hept-5-ene-2,3-dicarboximide; N-hydroxy-cis-cyclohexane-1,2-dicarboximide; N-hydroxy-cis-4-cyclohexene-1,2 dicarboximide; N-hydroxynaphthalimide sodium salt; N-hydroxy-o-benzenedisulphonimide; and N,N',N"-trihydroxyisocyanuric acid.

Non-limiting examples of suitable reaction conditions of the oxidizing step include a temperature from 70° C. to 200° C., such as 90° C. to 130° C., and a pressure of 50 kPa to 10,000 kPa. A basic buffering agent may be added to react with acidic by-products that may form during the oxidation. In addition, an aqueous phase may be introduced into the oxidation reactor. The reaction may take place in a batch or continuous flow fashion.

The reactor used for the oxidizing step may be any type of reactor that allows for the oxidation of cyclohexylbenzene by an oxidizing agent, such as molecular oxygen. A particularly advantageous example of the suitable oxidation reactor is a bubble column reactor capable of containing a volume of the reaction media and bubbling an $O_2$-containing gas stream (such as air) through the media. For example, the oxidation reactor may comprise a simple, largely open vessel with a distributor inlet for the oxygen-containing stream. The oxidation reactor may have means to withdraw a portion of the reaction media and pump it through a suitable cooling device and return the cooled portion to the reactor, thereby managing the heat generated in the reaction. Alternatively, cooling coils providing indirect cooling, e.g., by cooling water, may be operated within the oxidation reactor to remove at least a portion of the generated heat. Alternatively, the oxidation reactor may comprise a plurality of reactors in series, each operating at the same or different conditions selected to enhance the oxidation reaction of reaction media with different compositions. The oxidation reactor may be operated in a batch, semi-batch, or continuous flow manner well known to those skilled in the art.

Treatment of the Oxidation Product before Cleavage

Desirably, the oxidation product exiting the oxidation reactor contains cyclohexyl-1-phenyl-1-hydroperoxide at a concentration in a range from Chp1 wt % to Chp2 wt %, based on the total weight of the oxidation product, where Chp1 and Chp2 can be, independently, 5, 10, 15, 20, 25, 30, 35, 40, 45, 50, 55, 60, 65, 70, 75, 80, as long as Chp1<Chp2. The oxidation product may further comprise (i) an oxidation catalyst described above; and (ii) unreacted cyclohexylbenzene at a concentration in a range from Cchb1 wt % to Cchb2 wt %, based on the total weight of the oxidation product, where Cchb1 and Cchb2 can be, independently, 20, 25, 30, 35, 40, 45, 50, 55, 60, 65, 70, 75, 80, 85, 90, 95, as long as Cchb1<Cchb2.

In addition, the oxidation product may contain one or more hydroperoxides other than cyclohexyl-1-phenyl-1-hydroperoxide generated as a byproduct of the oxidation reaction of cyclohexylbenzene, or as the oxidation product of some oxidizable component other than cyclohexylbenzene that may have been contained in feed supplied to the oxidizing step, such as cyclohexyl-2-phenyl-1-hydroperoxide, and cyclohexyl-3-phenyl-1-hydroperoxide. These undesired hydroperoxides are desirably at a total concentration of at most 5 wt %, such as at most 3 wt %, 2 wt %, 1 wt %, or even 0.1 wt %.

The oxidation product contains the oxidation catalyst, such as NHPI, and certain by-products. Thus, it may be desirable to wash the oxidation product to remove the by-products and/or the catalyst before cleavage by using an aqueous dispersion. For example, a basic aqueous dispersion, such as a solution of one or more of alkali or alkali earth carbonates, alkali or alkali earth bicarbonates, alkali or alkali earth hydroxides, ammonium hydroxide, may be used to wash the oxidation product to extract NHPI or other similar imide-based catalysts from the oxidation product. In so doing, water concentration in the oxidation product thus washed will increase.

Alternatively, to reclaim the oxidation catalyst from the oxidation product, the oxidation product may be subjected to contacting with a solid sorbent in the form of particles in a slurry or a fixed bed, such as solid alkali or alkali earth metal carbonates, alkali or alkali earth metal bicarbonates, alkali or alkali earth metal hydroxide, molecular sieves, activated carbon, and the like. After separation, the sorbent may be washed using a polar solvent, such as water, acetone, an alcohol, and the like, to reclaim the oxidation catalyst, which can be purified and recycled to the oxidation reactor.

In the process of the present disclosure, at least a portion of the cyclohexylbenzene hydroperoxide in the oxidation product is subjected to a cleavage reaction, desirably in the presence of a catalyst such as an acid, whereby it is converted into phenol and/or cyclohexanone.

At least a portion of the oxidation product may be fed into the cleavage reactor without substantial alteration of the concentration of cyclohexylbenzene hydroperoxide and/or cyclohexylbenzene therein. Thus, where the concentration of cyclohexylbenzene in the oxidation product is CCHB(op) wt % based on the total weight of the oxidation product, and the concentration of cyclohexylbenzene in the cleavage feed is CCHB(cf) wt % based on the total weight of the cleavage feed before any material other than those contained in the oxidation product is added, the following relationship may be satisfied: $(CCHB(op)-CCHB(cf))/CCHB(cf) \leq 0.05$. Thus, the oxidation product may be flashed in a vessel at an absolute pressure in a range from Pf1 kPa to Pf2 kPa to remove a portion of water contained therein, where Pf1 and Pf2 can be, independently, 2.50, 2.67, 3.00, 3.50, 4.00, 4.50, 5.00, 5.50, 6.00, 6.50, 6.67, 7.00, 7.50, 8.00, 8.50, 9.00, 10.00, 11.00, 12.00, 13.00, 13.33, 14.00, 15.00, 16.00, 17.00, 18.00, 19.00, 20.00, 25.00, 30.00, 35.00, 40.00, 45.00, or 50.00, as long as Pf1<Pf2. Desirably, the oxidation product may be flashed in a vessel, such as a flashing drum, at an absolute pressure in a range from 6.67 kPa (50 torr) to 13.33 kPa (100 torr). During the flashing step, other low boiling components that may be present in the oxidation product, such as lower acids (e.g., formic acid, acetic acid, and the like) and low boiling point hydrocarbons (e.g., benzene, cyclohexane, methylcyclopentane, and the like), may be at least partially removed along with water, resulting in a cleaner cleavage feed.

Desirably, at least a portion of the oxidation product is not fed into the cleavage reactor before the concentration of cyclohexylbenzene therein is significantly reduced, and hence, the concentration of cyclohexylbenzene hydroperoxide is significantly increased. Thus, where the concentration of cyclohexylbenzene in the oxidation product is CCHB(op) wt % based on the total weight of the oxidation product, and the concentration of cyclohexylbenzene in the cleavage feed is CCHB(cf) wt % based on the total weight of the cleavage feed before any material other than those contained in the oxidation product is added, the following relationship may be satisfied: $R1<(CCHB(op)-CCHB(cf))/CCHB(op))<R^2$, where R1 and R2 are, independently, 0.05, 0.08, 0.10, 0.12, 0.14, 0.15, 0.18, 0.20, 0.25, 0.30, 0.35, 0.40, 0.45, 0.50, 0.55, 0.60, 0.70, 0.75, 0.80, 0.85, or even 0.90, as long as R1<R2. Desirably, R1=0.25, and R2=0.75. The reduction of cyclohexylbenzene concentration from the oxidation product before cleavage is particularly advantageous where liquid acid, such as sulfuric acid, is used as the cleavage catalyst. Without intending to be bound by a particular theory, it is believed that this is because the liquid acid tends to have low solubility in cyclohexylbenzene, and the desired catalytic effect of the liquid acid can be significantly reduced as a result of high cyclohexylbenzene concentration. Experimental data have shown that partial removal of cyclohexylbenzene concentration from the oxidation product before it is fed to the cleavage step can significantly improve the selectivity of the cleavage reaction to form the desired products, i.e., cyclohexanone and/or phenol.

Because cyclohexylbenzene hydroperoxide is prone to decomposition at an elevated temperature, e.g., at above 150° C., the removal of cyclohexylbenzene from the oxidation product should generally be conducted at a relatively low temperature, e.g., no higher than 150° C., or no higher than 140° C., or no higher than 130° C., or no higher than 120° C., or even no higher than 110° C. Cyclohexylbenzene has a high boiling point (239° C. at 101 kPa). Thus, at the acceptable cyclohexylbenzene-removal temperature, cyclohexylbenzene tends to have very low vapor pressure. Accordingly, to effectively remove a meaningful amount of cyclohexylbenzene from the oxidation product, the oxidation product may be subjected to a very low absolute pressure, e.g., in a range from Pc1 kPa to Pc2 kPa, where Pc1 and Pc2 can be, independently, 0.13, 0.15, 0.20, 0.25, 0.26, 0.30, 0.35, 0.39, 0.40, 0.45, 0.50, 0.60, 0.65, 0.70, 0.75, 0.80, 0.85, 0.90, 0.95, 1.00, 1.33, 1.50, 2.00, 2.50, 2.66, as long as Pc1<Pc2. Desirably, Pc1=0.27, and Pc2=2.00.

Where cyclohexylbenzene is partly removed from the oxidation product before cleavage, water contained in the oxidation product can be at least partly removed at the same time and in the same vessel where the cyclohexylbenzene is partly removed at a low absolute internal pressure.

Because of the very low absolute pressure required for effective cyclohexylbenzene removal, it is highly desired that before the oxidation product is subjected to cyclohexylbenzene removal, components with boiling points substantially lower than cyclohexylbenzene, such as water, benzene, cyclohexane, lower acids, and the like, contained in the oxidation product are removed at a relatively high pressure before the mixture is subjected to the very low pressure required for cyclohexylbenzene removal, such that the vacuum pump used for imparting the very low pressure is not overwhelmed. To that end, the oxidation product, upon exiting the oxidation reactor, may be first flashed in a first vessel such as a flashing drum at an absolute pressure in a range from Pf1 kPa to Pf2 kPa, where Pf1 and Pf2 can be, independently, 2.67, 3.00, 3.50, 4.00, 4.50, 5.00, 6.00, 7.00, 8.00, 9.00, 10.00, 11.00, 12.00, 13.00, 13.33, 14.00, 15.00, 20.00, 25.00, 30.00, 35.00, 40.00, 45.00, 50,00, as long as Pf1<Pf2, where a majority of the water contained in the oxidation product is removed, and desirably less than AA wt % of the cyclohexylbenzene contained in the oxidation product is removed, the percentage based on the total amount of cyclohexylbenzene contained in the oxidation product, where AA can be: 5, 4, 3, 2, 1, 0.8, 0.6, 0.5, 0.4, 0.3, 0.2, or 0.1.

Removal of cyclohexylbenzene from the oxidation product can be advantageously conducted in a concentrator comprising one or more falling film evaporator(s), such as those descried in co-pending, co-assigned U.S. provisional patent application Ser. No. 61/841,072 filed on Jun. 28, 2013 and entitled "Process for Concentrating a Mixture Containing Organic Hydroperoxide." The concentrator advantageously employs one or more falling film evaporators operating in parallel and/or in series operating under very low absolute pressure(s) described above. Because cyclohexylbenzene has a lower boiling point than cyclohexylbenzene hydroperoxide, a portion of the cyclohexylbenzene contained in the oxidation product evaporates under the very low pressure and is enriched in the vapor phase, condensed and collected for recycling back to the oxidizing step. Since by-products produced in the oxidizing step tend to accumulate in the condensed cyclohexylbenzene stream, a washing or extracting treatment of the condensed cyclohexylbenzene using an aqueous dispersion or other agent may be desired before the recycling thereof to the oxidizing step in order to prevent interference of the oxidation reaction of cyclohexylbenzene by the accumulated oxidation by-products. Such aqueous dispersion may be acidic, basic, or neutral in pH. The washing or extracting treatment may advantageously include a first step of chemical wash followed by a step of washing using water only. The thus washed reclaimed cyclohexylbenzene may be dried by using a water sorbent, such as, for example, a 3 Å molecular sieve before being recycled to oxidizing step. Alternatively, because water up to a certain amount is tolerated in the oxidation reactor, the thus washed cyclohexylbenzene, which contains a significant amount of water, may be fed to the oxidizing step directly without drying as at least a portion of the total feed, thus eliminating the cost of drying.

As an alternative approach, water removal of the optionally treated oxidation product can be effected by passing the liquid mixture through a water sorbent, such as a 3 Å molecular sieve. Desirably, the water sorbent also adsorbs the oxidation catalyst, which may be reclaimed by washing with a polar solvent.

Additionally or alternatively, after water removal and before or after partial cyclohexylbenzene removal, all or a portion of the oxidation product may be cooled to cause crystallization of the unreacted imide oxidation catalyst, which may then be separated either by filtration or by scraping from a heat exchanger surface used to effect the crystallization.

Cleavage Reaction

As discussed above, the process for making phenol and cyclohexanone from benzene includes cleaving at least a portion of the cyclohexylbenzene hydroperoxide contained in the oxidation product in the presence of an acid catalyst to produce a cleavage reaction mixture comprising the acid catalyst, phenol, and cyclohexanone. As used herein, "cleaving" means causing a cleavage reaction to occur. In the cleavage reaction, at least a portion of the desired cyclohexyl-1-phenyl-1-hydroperoxide desirably decomposes in high selectivity to cyclohexanone and phenol, and further, other hydroperoxides present may decompose to form various products, discussed below.

The acid catalyst may be at least partially soluble in the cleavage reaction mixture, stable at a temperature of at least 185° C. and has a lower volatility (higher normal boiling point) than cyclohexylbenzene.

Acid catalysts include, but are not limited to, Bronsted acids, Lewis acids, sulfonic acids, perchloric acid, phosphoric acid, hydrochloric acid, p-toluene sulfonic acid, aluminum chloride, oleum, sulfur trioxide, ferric chloride, boron trifluoride, sulfur dioxide, and sulfur trioxide. Sulfuric acid is a preferred acid catalyst.

As a result of potentially high amounts of cyclohexylbenzene in the cleavage reaction mixture, considerably higher than cumene in the Hock process material undergoing a cleavage reaction, it may be convenient in the present invention to use more acid catalyst to effect the cleavage reaction than typically believed optimal in the Hock process, to at least partially overcome the insolubility of the acid in the cleavage reaction mixture. However, lower amounts of acid catalyst may be applied in the present invention, with appropriate additional cleavage reactor volume and residence time of the cleavage reaction mixture in the cleavage reactor to obtain high hydroperoxide conversion.

The cleavage reaction may be conducted under cleavage conditions including a temperature of at least 20° C. and no greater than 200° C., or at least 40° C. and no greater than 120° C., and a pressure of at least 1 and no greater than 370 psig (at least 7 kPa, gauge and no greater than 2,550 kPa, gauge), or at least 14.5 psig and no greater than 145 psig (at least 100 kPa, gauge and no greater than 1,000 kPa, gauge) such that the cleavage reaction mixture is completely or predominantly in the liquid phase during the cleavage reaction.

Thus, the cleavage reaction mixture may contain the acid catalyst at a concentration in a range from Cac1 ppm to Cac2 ppm by weight of the total weight of the cleavage reaction mixture, where Cac1 and Cac2 can be, independently, 1, 2, 3, 4, 5, 6, 7, 8, 9, 10, 20, 30, 40, 50, 60, 80, 100, 150, 200, 250, 300, 350, 400, 450, 500, 600, 700, 800, 900, 1000, 1500, 2000, 2500, 3000, 3500, 4000, 4500, or even 5000, as long as Cac1<Cac2. Desirably, Cac1 is 10, and Cac2 is 200.

Conversion of any hydroperoxide, such as cyclohexyl-1-phenyl-1-hydroperoxide, and conveniently all cyclohexyl-1-phenyl-1-hydroperoxide and other hydroperoxides, may be very high in the cleavage reaction, e.g., at least 90.0 wt %, or at least 95.0 wt %, or at least 98.0 wt %, or at least 99.0 wt %, or at least 99.5 wt %, or at least 99.9 wt %, or even 100 wt %, the percentage conversion based on the weight of a given specie of hydroperoxide, or of all cyclohexyl-1-phenyl-1-hydroperoxide, and other hydroperoxides present in the at least a portion of the oxidation product undergoing the cleavage reaction. This is desirable because any hydroperoxide, even the cyclohexyl-1-phenyl-1-hydroperoxide, becomes a contaminant in the cleavage reaction mixture and treated cleavage reaction mixture, discussed below. Hydroperoxides cause undesired chemistry when decomposed under uncontrolled conditions outside the cleavage reaction, or if thermally decomposed under the conditions in a distillation column.

The major products of the cleavage reaction of cyclohexyl-1-phenyl-1-hydroperoxide are phenol and cyclohexanone according to the following desired Reaction-12:

(Reaction-12)

Desirably, each mole of cyclohexyl-1-phenyl-1-hydroperoxide produces one mole of phenol and one mole of cyclohexanone. However, due to side reactions, the selectivity of the cleavage reaction of phenol can range from Sph1% to Sph2% and the selectivity of cyclohexanone can range from Sch1% to Sch2%, where Sph1, Sph2, Sch1, and Sch2 can be, independently, 85, 87, 88, 89, 90, 91, 92, 93, 94, 95, 96, 97, 98, 99, or even 99.5, as long as Sph1<Sph2, and Sch1<Sch2.

Besides the cleavage feed comprising cyclohexylbenzene hydroperoxide, cyclohexylbenzene and other components originating directly from the oxidation product, the cleavage reaction mixture may further comprise other added materials, such as the cleavage catalyst, a solvent, and one or more products of the cleavage reaction such as phenol and cyclohexanone recycled from the cleavage reaction effluent, or from a downstream separation step. Thus, the cleavage reaction mixture inside the cleavage reactor may comprise, based on the total weight of the cleavage reaction mixture: (i) phenol at a concentration from Cph1 wt % to Cph2 wt %, where Cph1 and Cph2 can be, independently, 20, 25, 30, 35, 40, 45, 50, 55, 60, 65, 70, 75, or 80, as long as Cph1<Cph2; (ii) cyclohexanone at a concentration from Cch1 wt % to Cch2 wt %, where Cch1 and Cch2 can be, independently, 20, 25, 30, 35, 40, 45, 50, 55, 60, 65, 70, 75, or 80, as long as Cch1<Cch2; (iii) cyclohexylbenzene at a concentration from Cchb1 wt % to Cchb2 wt %, where Cchb1 and Cchb2 can be, independently, 5, 8, 9, 10, 12, 14, 15, 18, 20, 22, 24, 25, 26, 28, 30, 35, 40, 45, 50, 55, 60, 65, 70, as long as Cchb1<Cchb2.

As used herein, a "contaminant" or a "contaminant byproduct" may include any unwanted hydrocarbon or oxygenated hydrocarbon component in the cleavage reaction mixture or the neutralized cleavage mixture, or any portion of either; that is anything other than phenol, cyclohexanone, and cyclohexylbenzene. They are unwanted because their presence indicates a decreased yield of desired product phenol and cyclohexanone from cyclohexylbenzene, or they cause difficulties in the separation and purification of phenol, cyclohexanone or unconverted cyclohexylbenzene, or some combination thereof. A contaminant in the cleavage reaction mixture, or the neutralized cleavage mixture, or any portion thereof may have been produced in any element of the present invention, or may have been contained in the feed comprising cyclohexylbenzene undergoing oxidation. For example, a contaminant may be present in the cleavage reaction mixture as a result of one or more of: (i) it was included with the cyclohexylbenzene (e.g., as a byproduct of production using hydroalkylation or alkylation); (ii) it was produced in oxidation of the feed comprising cyclohexylbenzene, and potentially the oxidation of an oxidizable component from (i); and/or (iii) it was produced in the cleavage reaction of at least a portion of the oxidation product from (ii).

The reactor used to effect the cleavage reaction (i.e., the cleavage reactor) may be any type of reactor known to those skilled in the art. For example, the cleavage reactor may be a simple, largely open vessel operating in a near-continuous stirred tank reactor mode, or a simple, open length of pipe operating in a near-plug flow reactor mode. Alternatively, the cleavage reactor comprises a plurality of reactors in series, each performing a portion of the conversion reaction, optionally operating in different modes and at different conditions selected to enhance the cleavage reaction at the pertinent conversion range. For example, the cleavage reactor can be a catalytic distillation unit.

The cleavage reactor may be operable to transport a portion of the contents through a cooling device and return the cooled portion to the cleavage reactor, thereby managing the exothermicity of the cleavage reaction. Alternatively, the reactor may be operated adiabatically. For example, cooling coils operating within the cleavage reactor(s) remove at least a portion of heat generated.

The cleavage reaction product exiting cleavage reactor may comprise, based on the total weight of the cleavage reaction mixture: (i) phenol at a concentration from Cph3 wt % to Cph4 wt %, where Cph1 and Cph2 can be, independently, 20, 25, 30, 35, 40, 45, 50, 55, 60, 65, 70, 75, or 80, as long as Cph3<Cph4; (ii) cyclohexanone at a concentration from Cch3 wt % to Cch4 wt %, where Cch3 and Cch4 can be, independently, 20, 25, 30, 35, 40, 45, 50, 55, 60, 65, 70, 75, or 80, as long as Cch3<Cch4; (iii) cyclohexylbenzene at a concentration from Cchb3 wt % to Cchb4 wt %, where Cchb3 and Cchb4 can be, independently, 5, 8, 9, 10, 12, 14, 15, 18, 20, 22, 24, 25, 26, 28, 30, 35, 40, 45, 50, 55, 60, 65, 70, as long as Cchb3<Cchb4.

At least a portion of the cleavage reaction mixture may be subjected to a neutralization reaction, which may include all or some fraction of the cleavage reaction mixture as directly produced without undergoing any separation (e.g., some fraction resulting from diverting some amount of the cleavage reaction mixture as directly produced to another disposition, such as temporary storage). Thus, the at least a portion of the cleavage reaction mixture may have the same composition as the cleavage reaction mixture. Further, all or some of the cleavage reaction mixture as directly produced may undergo one or more separations, and an appropriate product of that separation (or separations), now modified in composition relative the cleavage reaction mixture as directly produced, may provide the at least a portion of the cleavage reaction mixture subjected to the neutralization reaction.

The cyclohexylbenzene contained in the cleavage reaction product can be separated from other major components, such as phenol and cyclohexanone by, e.g., distillation. The separated cyclohexylbenzene can then be treated and/or purified, e.g., by washing using an aqueous dispersion, before being delivered to the oxidation step along with cyclohexylbenzene supplied from other resources, such as fresh cyclohexylbenzene produced from the hydroalkylation reactor and a recycle cyclohexylbenzene stream from the cyclohexylbenzene hydroperoxide concentrator.

Contaminant Treatment

As discussed above, the cleavage reaction mixture may comprise one or more contaminants. The processes may further comprise contacting at least a portion of a contaminant with an acidic material to convert at least a portion of the contaminant to a converted contaminant, thereby producing a modified reaction mixture. Detailed description of the contaminant treatment process can be found, e.g., in International Publication WO2012/036822A1, the relevant content of which is incorporated herein by reference in its entirety.

Uses of Cyclohexanone and Phenol

The cyclohexanone produced through the processes disclosed herein may be used, for example, as an industrial solvent, as an activator in oxidation reactions and in the production of adipic acid, cyclohexanone resins, cyclohexanone oxime, caprolactam, and nylons, such as nylon-6 and nylon-6,6.

The phenol produced through the processes disclosed herein may be used, for example, to produce phenolic resins, bisphenol A, ε-caprolactam, adipic acid, and/or plasticizers.

EXAMPLES

Reactor setup and catalyst loading employed in the examples of the current disclosure is provided as follows.

Catalyst activation and the hydroalkylation performance tests with the resulting activated catalyst samples were performed in down-flow 0.5" diameter stainless steel fixed bed reactors that were equipped with three-point thermocouples positioned at the center of the reactors. The 4.5" (11.43 cm) long catalyst beds were positioned to ensure that the three thermocouples (placed 2" (5.08 cm) apart) measured the temperatures at the inlet, outlet, and the center of the catalyst beds. In order to reduce the volumetric heat release and thus to afford more isothermal operations, the catalysts were diluted with quartz sand. The diluent also enhanced the even distribution of the activation feed and the hydroalkylation reactants in the catalyst bed. Neat quartz sand was used at either side of the catalyst bed. It served to preheat and evenly distribute the feed at the feed inlet side and to hold the catalyst bed at the exit side, the latter of which was at the bottom of the reactor (down-flow).

The reactors were encased in a 6" (15.24 cm) long 1" (2.54 cm) diameter brass sleeve that were centered along the catalyst beds to improve their temperature control. In the brass sleeves, there were three thermocouples positioned at the two ends and the center of the catalyst beds. The reactors were heated by three-zone clam-shell electrical furnaces. During steady-state operations, the temperatures of the three furnace zones were controlled by utilizing the feedback from the three thermocouples in the brass sleeves of the reactors. The catalyst bed temperatures at the three thermocouples were typically within 2° C. of the set values. The reported reaction temperatures (Trxn) were calculated as the weighted average of the three thermocouple measurements (Tinlet, Tmiddle, Toutlet) by the following formula:

$$Trxn = (Tinlet + 2Tmiddle + Toutlet)/4.$$

The catalysts in all experiments nominally consisted of 0.15 wt % Pd supported on alumina-bound MCM-49 (alumina/MCM-49 of 20/80 wt/wt). The catalysts were received in their calcined forms as 1/20" (1.27 mm) extrudates and were stored in closed plastic bottles. Before charging them into the reactors, the catalyst extrudates were broken up and sized to a length/diameter (L/D) ratio of near one (14-20 mesh) to provide reactor beds with proper hydrodynamics. As mentioned above, the catalysts were also diluted with quartz sand that on one hand reduced volumetric catalyst charge and thus volumetric heat release while also improving the desired plug-flow characteristics of the reactant streams passing through the catalyst beds.

In a typical hydroalkylation test, 1.7-2.1 g of 14-20 mesh catalyst diluted with 6 g quartz was charged into the reactor. After pressure testing, the catalysts were activated by a process that involved co-feeding benzene with hydrogen. The treatments were performed at 165 psig (1138 kPa gauge pressure; 1239 kPa absolute pressure) by ramping the reactor temperature up to a 240° C. nominal value at 5° C./hour ramp rate then holding it there for 2-3 hours. The hydrogen flow rates during activation corresponded to 1200-1 300 volume $H_2$/volume catalyst/hour (or 1200-1300/hour) gas hourly space velocity (GHSV). The benzene flow rates during activation corresponded to 2.5 weigh benzene/weight catalyst/hour (or 2.5/hour) weight hourly space velocity (WHSV). The nominal $H_2$/benzene ratio was 4 mol/mol. The activation was finished by letting the catalyst cool down to near the hydroalkylation temperature (145° C.) while keeping the pressure and feed flow rates unchanged. The catalyst then was brought on HA stream by adjusting the benzene and hydrogen flow rates to their initial HA test values corresponding to 0.7 mol/mol $H_2$/benzene and 2.5/hour benzene WHSV. In both instances, catalyst activity was so high that the reaction became $H_2$ limited necessitating an increase to ultimately 5/hour benzene WHSV.

After letting the reactors line out for about 6 hours, the product effluents were periodically directed to a chilled knock out vessels held at −5° C. and liquid samples were collected then analyzed by a gas chromatograph equipped with a flame-ionization detector (FID). The response factors for the various product components were determined either by using blends of authentic samples or by using factors published in the J. of Gas Chromatography in February 1967, p68 by W. A. Dietz. Calibrations were checked by analyzing gravimetrically prepared calibration blends. Benzene conversion and product selectivity were determined from the normalized FID areas by applying the calibration response factors. The results are listed in TABLE I below, where CE-1 is a comparative catalyst with no detectable 2θ peak on XRD diagram at location of 9.5±0.5 degrees, and IE-1 is an inventive catalyst with an appreciable 2θ peak at location of 9.5±0.5 degrees. The following abbreviations are used in the present disclosure, including the drawings, tables, and the texts of the specification:

TOS: time on stream
CHB: cyclohexylbenzene
C18: 18-carbon fraction, primarily comprising dicyclohexylbenzene
Chex: cyclohexane
MCP: methylcyclopentane
WHSV: weight hourly space velocity expressed as (weight of material)/(weight of catalyst times time in hour)

TABLE I

| Catalyst | Benzene WHSV (1/hour) | Benzene Conversion (%) | Selectivity | | | |
|---|---|---|---|---|---|---|
| | | | Chex (%) | MCP (%) | CHB (%) | C18 (%) |
| CE-I (Comparative) | 5.0 | 36 | 6.0 | 0.10 | 75.2 | 16.3 |
| IE-1 (Inventive) | 4.9 | 34 | 5.8 | 0.04 | 79.6 | 12.4 |

As the results in TABLE I show, the currently disclosed improved hydroalkylation catalyst yielded more CHB and less by-products, particularly less over-alkylated products (C18) at comparable benzene conversion as compared to the yields with the comparative catalyst. In fact, the over-alkylated C18 yield with the inventive catalyst was 24% less (12.4% vs. 16.3%) than the C18 byproduct yield with the comparative sample.

Another series of tests were carried out in which the comparative and currently disclosed catalysts were activated at the same 240° C. temperature, but in the absence of benzene. The tests were carried out in 12" diameter down-flow reactors. The catalysts were sieved to 60/100 mesh particle size then were mixed with 100 mesh quartz to keep the feed flow over the catalyst as uniform as possible and to improve temperature control and isothermal catalyst bed profile during hydroalkylation. The catalysts were activated by flowing 50 standard mL/min hydrogen over the catalyst and by ramping up temperature at 5° C./hour to 240° C. and maintaining the catalyst bed at that temperature for 12 hours. Reactor pressure during activation was 50 psig (345 kPa gauge pressure; 446 kPa absolute pressure).

After the catalysts were activated, they were tested for their benzene hydroalkylation performance at 2.9/hour and/or 4.1/hour benzene WHSV, 145° C., and 165 psig total pressure (1138 kPa gauge pressure; 1239 kPa absolute pressure). The $H_2$/benzene feed molar ratio was 0.7.

The effluent from the reactor was condensed and analyzed by an off-line gas chromatograph (GC) with a Petrocol 150 m boiling point column. Results from the tests are summarized in TABLE II below, where comparative catalyst CE-2 does not have a 2θ peak at 9.5±0.5 degrees in an XRD diagram, and the inventive catalysts IE-2 and IE-3 both have appreciable 2θ peaks at 9.5±0.5 degrees in XRD diagrams.

TABLE II

| Catalyst | Benzene WHSV (1/hour) | Benzene Conversion (%) | Selectivity | | |
|---|---|---|---|---|---|
| | | | Chex (%) | CHB (%) | DiCHB (%) |
| CE-2 (Comparative) | 2.9 | 30.5 | 4.8 | 77.2 | 13.9 |
| IE-2 (Inventive) | 2.9 | 42.6 | 7.0 | 74.4 | 14.6 |
| IE-3 (Inventive) | 4.1 | 33.6 | 6.4 | 77.5 | 12.1 |

As can be seen from the TABLE II, the inventive hydroalkylation catalyst comprising FERR performed well. It showed nearly 43% conversion at 3/hour benzene WHSV. This compares favorably with 31% conversion shown by the comparative catalyst CE-2. At 34% conversion (4.1/hour WHSV), the inventive catalyst IE-3 showed 6.4% selectivity toward cyclohexane, which is somewhat higher than the 4.8% selectivity to cyclohexane shown by the comparative catalyst CE-2. However, the cyclohexane byproduct can be readily dehydrogenating back to benzene at nearly stoichiometric yields. At comparable conversion, the dicyclohexylbenzene selectivity of the inventive catalyst IE-3 is 12%, which is significantly lower than that of the comparative catalyst CE-2.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The contents of all references cited herein are incorporated by reference in their entirety.

Non-limiting embodiments of the processes of the present disclosure include:

E1. A catalyst comprising
(A) an aluminosilicate molecular sieve comprising a ferrierite phase; and
(B) a hydrogenation metal component.

E2. The catalyst of E1, wherein the ferrierite phase has a concentration in a range from 0.001 wt % to 5.0 wt % of the total weight of the molecular sieve.

E3. The catalyst of E2, wherein the ferrierite phase has a concentration in a range from 0.01 wt % to 0.50 wt % of the total weight of the molecular sieve.

E4. The catalyst of any of E1 to E3, wherein the molecular sieve is of the MWW type.

E5. The catalyst of E4, wherein the molecular sieve is of the MCM-22 type.

E6. The catalyst of any of E1 to E5, wherein the molecular sieve exhibits an X-ray diffraction pattern including d-spacing maxima at 12.4±0.25, 6.9±0.15, 3.57±0.07, and 3.42±0.07 Angstrom.

E6A. The catalyst of any of E1 to E6, wherein the catalyst comprises at least one of Na, K, Ca, and Mg at a concentration expressed on the basis of the total weight of the molecular sieve in a range from 10 ppm by 5000 ppm.

E6B. The catalyst of any of the preceding paragraphs E1 to E6A, wherein the catalyst comprises Na at a concentration expressed on the basis of the total weight of the molecular sieve in a range from 10 ppm by 5000 ppm.

E6C. The catalyst of E6B, comprising any of K, Ca, and Mg at a concentration expressed on the basis of the total weight of the molecular sieve not higher than 100 ppm, or not higher than 50 ppm, or not higher than 30 ppm, or not higher than 30 ppm, or not higher than 10 ppm, or not higher than 5 ppm.

E7. The catalyst of any of E1 to E6, wherein the molecular sieve exhibits an X-ray diffraction peak 2θ at 9.5±0.5 degrees.

E8. The catalyst of E1 to E7, wherein the hydrogenation metal component is selected from Co, Ni, Ru, Rh, Pd, Re, Os, Ir, Pt, and mixtures and combinations thereof E9. The catalyst of any of E1 to E8, further comprising an inorganic oxide support component.

E10. The catalyst of E9, wherein the inorganic oxide support component comprises at least one of $Al_2O_3$, $SiO_2$, $TiO_2$, $ZrO_2$, and mixtures and combinations thereof E11. The catalyst of E9 or E10, wherein the amount of the inorganic oxide support component is in a range from 1 wt % to 30 wt % of the total weight of the catalyst.

E12. The catalyst of E10 or E11, wherein the inorganic oxide support component comprises $Al_2O_3$ and/or $SiO_2$.

E13. The catalyst of E12, wherein the inorganic oxide support component is $Al_2O_3$.

E14. The catalyst of E9 to E13, wherein the inorganic oxide support component has an average particle size in a range from 1 μm to 70 μm.

E15. The catalyst of any of E9 to E14, wherein the inorganic oxide support component has an average particle size in a range from 5 μm to 40 μm.

E16. The catalyst of any of E1 to E15, wherein the amount of the hydrogenation metal component is in a range from 0.01 wt % to 5.0 wt % of the total weight of the catalyst.

E17. The catalyst of E16, wherein the amount of the hydrogenation metal component is in a range from 0.05 wt % to 1.00 wt % of the total weight of the catalyst.

E18. The catalyst of any of E9 to E17, wherein at least 50 wt % of the hydrogenation metal component is distributed on the inorganic oxide support component.

E19. The catalyst of any of E1 to E19, wherein the molecular sieve is selected from the group of MCM-22, SSZ-25, ERB-1, PSH-3, ITQ-1, ITQ-2, MCM-36, MCM-49, MCM-56, and mixtures and combinations thereof.

E20. A hydroalkylation process comprising:
contacting a first aromatic compound with hydrogen in the presence of a catalyst according to any of the preceding E1 to E19 under hydroalkylation conditions to produce an alkylated aromatic compound.

E21. The process of E20, wherein the first aromatic compound has a molecular structure of the formula (F-I) below:

(F-I)

where:
R¹, the same or different at each occurrence, represents a substituted or unsubstituted linear, branched acyclic, or cyclic alkyl or alkenyl group having from 1 to 20 carbon atoms (such as 1 to 10, or 1 to 5 carbon atoms); and
m is an integer from 0 to 5.

E22. The process of E21, wherein the alkylated aromatic compound is represented by the following general formula (F-II):

(F-II)

where:
R² and R³, the same or different at each occurrence, each independently represents a substituted or unsubstituted linear, branched acyclic, or cyclic alkyl or alkenyl having from 1 to 20 carbon atoms (such as from 1 to 10, or from 1 to 5); and
o and p are independently integers from 0 to 5.

E23. The process of E22, wherein the first aromatic compound is selected from benzene, toluene, ethylbenzene, n-propylbenzene, cumene, o-xylene, m-xylene, p-xylene, o-methylethylbenzene, m-methylethylbenzene, and p-methylethylbenzene.

E24. The process of E22 or E23, wherein the alkylated aromatic compound is selected from:
cyclohexylbenzene;
methylcyclohexyltoluene;
methylcyclohexyl-ethylbenzene;
ethylcyclohexyl-ethylbenzene;
propylcyclohexyl-propylbenzene;
butylcyclohexyl-butylbenzene;
dimethylcyclohexyl-dimethylbenzene;
diethylcyclohexyl-diethylbenzene;
trimethylcyclohexyl-trimethylbenzene;
isopropylcyclohexylcumene;
methylethylcyclohexyl-methylethylbenzene; and
combinations and mixtures of at least two thereof.

E25. The process of E24, wherein the first aromatic compound is benzene and the alkylated aromatic compound is cyclohexylbenzene.

E26. The process of any of E20 to E25, wherein the hydroalkylation conditions comprise a temperature in a range from 90° C. to 180° C., an absolute pressure in a range from 100 kPa to 5000 kPa, and a molar ratio of hydrogen to the first aromatic compound in a range from 0.01 to 100.

E27. The process of any of E20 to E26, wherein the first aromatic compound is benzene, and the hydroalkylation conditions comprise a temperature in a range from 90° C. to 180° C., an absolute pressure in a range from 100 kPa to 5000 kPa, and a molar ratio of hydrogen to the first aromatic compound in a range from 0.01 to 10.

E28. A process for making phenol and/or cyclohexanone, the process comprising:
(A) contacting benzene with hydrogen in the presence of a catalyst of any of the preceding E1 to E19 under hydroalkylation conditions to obtain a hydroalkylation product comprising cyclohexylbenzene;
(B) oxidizing at least a portion of the cyclohexylbenzene in the hydroalkylation product to obtain an oxidation product comprising cyclohexylbenzene hydroperoxide; and
(C) cleaving at least a portion of the cyclohexylbenzene hydroperoxide in the oxidation product in the presence of an acid cleavage catalyst to obtain a cleavage product comprising phenol and cyclohexanone.

E29. The process of E28, wherein in step (A), the hydroalkylation conditions comprise a temperature in a range from 90° C. to 180° C., an absolute pressure in a range from 100 kPa to 5000 kPa, and a molar ratio of hydrogen to the first aromatic compound in a range from 0.01 to 10.

The invention claimed is:
1. A catalyst comprising:
(A) an aluminosilicate molecular sieve comprising a ferrierite phase; and
(B) a hydrogenation metal component.

2. The catalyst of claim 1, wherein the ferrierite phase has a concentration in a range from 0.001 wt % to 5.0 wt % of the total weight of the molecular sieve.

3. The catalyst of claim 1, wherein the molecular sieve is of the MWW type.

4. The catalyst of claim 1, wherein the molecular sieve exhibits an X-ray diffraction pattern including d-spacing maxima at 12.4±0.25, 6.9±0.15, 3.57±0.07, and 3.42±0.07 Angstrom.

5. The catalyst of claim 1, wherein the molecular sieve exhibits an X-ray diffraction peak 2θ at 9.5±0.5 degrees.

6. The catalyst of claim 1, wherein the hydrogenation metal component is selected from Co, Ni, Ru, Rh, Pd, Re, Os, Ir, Pt, and mixtures and combinations thereof 7. The catalyst of claim 1, further comprising an inorganic oxide support component.

8. The catalyst of claim 7, wherein the inorganic oxide support component comprises at least one of $Al_2O_3$, $SiO_2$, $TiO_2$, $ZrO_2$, and mixtures and combinations thereof.

9. The catalyst of claim 7, wherein the amount of the inorganic oxide support component is in a range from 1 wt % to 30 wt % of the total weight of the catalyst.

10. The catalyst of claim 7, wherein the inorganic oxide support component has an average particle size in a range from 1 μm to 70 μm.

11. The catalyst of claim 1, wherein the amount of the hydrogenation metal component is in a range from 0.01 wt % to 5.0 wt % of the total weight of the catalyst.

12. The catalyst of claim 7, wherein at least 50 wt % of the hydrogenation metal component is distributed on the inorganic oxide support component.

13. The catalyst of claim 1, wherein the molecular sieve is selected from the group of MCM-22, SSZ-25, ERB-1, PSH-3, ITQ-1, ITQ-2, MCM-36, MCM-49, MCM-56, and mixtures and combinations thereof.

14. A hydroalkylation process comprising:
contacting a first aromatic compound with hydrogen in the presence of a hydroalkylation catalyst under hydroalky- lation conditions to produce an alkylated aromatic compound, wherein the hydroalkylation catalyst comprises an aluminosilicate molecular sieve comprising a ferrierite phase; and a hydrogenation metal component.

15. The process of claim 14, wherein the first aromatic compound has a molecular structure of the formula (F-I) below:

(F-I)

where:
$R^1$, the same or different at each occurrence, represents a substituted or unsubstituted linear, branched acyclic, or cyclic alkyl or alkenyl group having from 1 to 20 carbon atoms; and
m is an integer from 0 to 5.

16. The process of claim 15, wherein the alkylated aromatic compound is represented by the following general formula (F-II):

(F-II)

where:
$R^2$ and $R^3$, the same or different at each occurrence, each independently represents a substituted or unsubstituted linear, branched acyclic, or cyclic alkyl or alkenyl having from 1 to 20 carbon atoms; and
o and p are independently integers from 0 to 5.

17. The process of claim 16, wherein the first aromatic compound is selected from benzene, toluene, ethylbenzene, n-propylbenzene, cumene, o-xylene, m-xylene, p-xylene, o-methylethylbenzene, m-methylethylbenzene, and p-methylethylbenzene.

18. The process of claim 16, wherein the alkylated aromatic compound is selected from:
cyclohexylbenzene;
methylcyclohexyltoluene;
methylcyclohexyl-ethylbenzene;
ethylcyclohexyl-ethylbenzene;
propylcyclohexyl-propylbenzene;
butylcyclohexyl-butylbenzene;
dimethylcyclohexyl-dimethylbenzene;
diethylcyclohexyl-diethylbenzene;
trimethylcyclohexyl-trimethylbenzene;
isopropylcyclohexylcumene;
methylethylcyclohexyl-methylethylbenzene; and
combinations and mixtures of at least two thereof.

19. The process of claim 17, wherein the first aromatic compound is benzene and the alkylated aromatic compound is cyclohexylbenzene.

20. The process of claim 14, wherein the hydroalkylation conditions comprise a temperature in a range from 90° C. to 180° C., an absolute pressure in a range from 100 kPa to 5000 kPa, and a molar ratio of hydrogen to the first aromatic compound in a range from 0.01 to 100.

21. The process of claim 14, wherein the first aromatic compound is benzene, and the hydroalkylation conditions comprise a temperature in a range from 90° C. to 180° C., an absolute pressure in a range from 100 kPa to 5000 kPa, and a molar ratio of hydrogen to the first aromatic compound in a range from 0.01 to 10.

22. A process for making phenol and/or cyclohexanone, the process comprising:
(A) contacting benzene with hydrogen in the presence of a hydroalkylation catalyst under hydroalkylation conditions to obtain a hydroalkylation product comprising cyclohexylbenzene;
wherein the hydroalkylation catalyst comprises an aluminosilicate molecular sieve comprising a ferrierite phase; and a hydrogenation metal component;
(B) oxidizing at least a portion of the cyclohexylbenzene in the hydroalkylation product to obtain an oxidation product comprising cyclohexylbenzene hydroperoxide; and
(C) cleaving at least a portion of the cyclohexylbenzene hydroperoxide in the oxidation product in the presence of an acid cleavage catalyst to obtain a cleavage product comprising phenol and cyclohexanone.

23. The process of claim 22, wherein in step (A), the hydroalkylation conditions comprise a temperature in a range from 90° C. to 180° C., an absolute pressure in a range from 100 kPa to 5000 kPa, and a molar ratio of hydrogen to the first aromatic compound in a range from 0.01 to 10.

* * * * *